United States Patent
van de Zande

(10) Patent No.: US 7,601,502 B2
(45) Date of Patent: Oct. 13, 2009

(54) PRIME BOOST VACCINE FOR THE PROTECTION OF EQUINES AGAINST EQUINE INFLUENZA

(75) Inventor: Saskia van de Zande, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 12/092,164

(22) PCT Filed: Oct. 27, 2006

(86) PCT No.: PCT/EP2006/067859

§ 371 (c)(1),
(2), (4) Date: Apr. 30, 2008

(87) PCT Pub. No.: WO2007/051763

PCT Pub. Date: May 10, 2007

(65) Prior Publication Data

US 2008/0292659 A1    Nov. 27, 2008

(30) Foreign Application Priority Data

Nov. 1, 2005    (EP) ................................. 05110231

(51) Int. Cl.
*C12Q 1/68*    (2006.01)
(52) U.S. Cl. .......................................... 435/6; 435/7.1
(58) Field of Classification Search .................. 435/6, 435/7.1

See application file for complete search history.

(56) References Cited

U.S. PATENT DOCUMENTS 4,693,893 A * 9/1987 Campbell ................. 424/206.1
7,226,604 B2 * 6/2007 Mellencamp ............ 424/229.1

OTHER PUBLICATIONS

T.M. Chambers, et al., Equine Veterinary Journal, 33:7 pp. 630-636, 2001.
European Medicines Agency: Committee for Medicinal Products for Veterinary Use, European Public Assessment Report (EPAR), Equilis Prequenza Te, Abstract, (2005).
European Medicines Agency: Summary of Product Characteristics, Equilis Prequenza Te (2006).
J.M. Minke, et al., Veterinary Research, 35, pp. 425-443, (2004).
J. Slater, et al., Veterinary Clinics of North America: Equine Practice, 16:1 pp. 49-68, (2000).
H.G.G. Townsend, et al., Equine Veterinary Journal, 33:7, pp. 637-643, (2001).

* cited by examiner

*Primary Examiner*—Ali R. Salimi
(74) *Attorney, Agent, or Firm*—William M. Blackstone

(57) ABSTRACT

The present invention is concerned with vaccinating equines against the equine influenza virus (EIV). It has now been found that adequate protection against equine influenza in equines can be achieved when vaccination with a live equine influenza vaccine (prime) is followed by vaccination with an inactivated influenza vaccine (boost), wherein the two shots are given no longer than 8 weeks apart.

3 Claims, No Drawings

PRIME BOOST VACCINE FOR THE PROTECTION OF EQUINES AGAINST EQUINE INFLUENZA

PRIORITY CLAIM TO RELATED PATENT APPLICATIONS

This patent claims priority under 35 U.S.C. §371 as a national phase of International Patent Application No. PCT/EP2006/067859 (filed Oct. 27, 2006); and published on May 10, 2007, as International Publication No. WO 2007/051763), which, in turn, claims priority to European Patent Application No. 05110231.7 (filed Nov. 1, 2005). The entire text of each of the above-referenced patent applications is hereby incorporated by referenced into this patent.

The present invention is concerned with vaccinating equines against the equine influenza virus (EIV).

Equine influenza is a major respiratory viral disease that causes flu like symptoms in equines. This disease is present throughout Europe, North America and parts of Asia. Disease symptoms caused by equine influenza virus can be severe, and are often followed by secondary bacterial infections which can lead to pneumonia and other problems. Horses of all ages are susceptible but infection is most common in young unvaccinated horses. Most horses exposed to the virus will show signs within a period of 1-5 days and recover after 2-3 weeks.

Explosive outbreaks have been seen in susceptible populations. The virus can be spread easily from horse to horse as a result of droplets and also from nasal discharge and from things like infected brushes and rugs. The disease is very contagious and there is almost 100% infection rate in a population that has been previously unexposed to the virus. This often follows the import of infected horses from endemic areas not showing clinical signs, and is worsened by the fact that international transport of horses is increasing.

Equine influenza virus was discovered in horses around 1956 when it was recovered during an epidemic of respiratory disease among horses in Eastern Europe (Sovinová O. et al., Acta. Virol., 2, 51-61, 1958) The virus, A/Equine/Prague/1/56, (H7N7), is now designated as the prototype virus for equine influenza subtype-1. In 1963 another influenza virus, now designated subtype-2, was discovered during a major outbreak in the United States (Waddell G. H. et al., J. Am. Vet. Med. Assoc., 143, 587-590, 1963). For subtype-2, the prototype virus is A/Equine/Miami/1/63 (H3N8). The H3N8 subtype has meanwhile spread over the world and, at present, is the predominant virus subtype (The H7N7 subtype has not been isolated since 1980). The H3N8 subtype is prone to antigenic drift. Various variants of the H3N8 subtype co-circulate. Especially isolates circulating in Europe and the USA were antigenically distinguishable, the European lineage is represented by A/eq/newmarket1/93 (N/1/93) and the US lineage is represented by A/eq/Newmarket/2/93 (N/2/93) viruses (both Newmarket viruses were isolated from samples taken on the same day from vaccinated 2 year old Thoroughbred horses that has pyrexia and occasional coughing) (Daly et al., Vaccine 22, 4101-4109, 2004).

The prevention of equine influenza largely depends on vaccination. Vaccines based on the virus need to be updated regularly in order to reflect the most recent epidemiological situation. It has been recommended that vaccines for equine influenza contain a representative H3N8 from both the American and European lineages.

The majority of vaccines for protecting equines against infection with equine influenza virus are adjuvated inactivated vaccines based on whole virus.

Reasonably effective vaccines, based on the two most important types of this virus, are available, but equines need to be vaccinated 2-3 times per year to ensure their immune status. However, the efficacy of inactivated (killed) virus vaccines is not always sufficient, and some times does not provide adequate protection for equines. Some inactivated vaccines can even produce undesirable side effects, for example, inflammatory reactions at the site of injection. Furthermore, inactivated vaccines are often not able to overcome maternal immunity in young foals, and can induce tolerance in a younger animal. Inactivated vaccines contain viral strains representing the "American type" equine influenza virus as well as the "European type" of the virus and need to be updated yearly with new strains as recommended each year by the WHO/OIE.

An attenuated live vaccine for equine influenza was developed by Heska. This vaccine Flu Avert IN was introduced by Heska in the United States in November 1999. Flu Avert I.N. vaccine is a "modified live" vaccine which incorporates a "cold adapted" virus that replicates only in the upper regions of the horse's respiratory system, but the virus does not replicate at the higher temperatures found in the lungs or lower respiratory tract of the animal. Heska's vaccine can be administered using a nasal applicator, rather than a needle. The cold-adapted virus strains were developed at the University of Pittsburgh by Drs. Patricia W. Dowling and Julius S. Youngner (U.S. Pat. No. 6,177,082 B1).

However, there is a continuing need for yet improved vaccines to protect equines against infection with Equine influenza.

It has now been found that adequate protection against equine influenza in equines can be achieved when vaccination with a live equine influenza vaccine (prime) is followed by vaccination with an inactivated influenza vaccine (boost), wherein the two shots are given no longer than 8 weeks apart.

The present invention therefore provides a method for vaccination of animals against equine influenza, wherein an animal is first vaccinated with a (prime) vaccine comprising an attenuated equine influenza virus, followed by a vaccination with a (boost) vaccine comprising an inactivated equine influenza virus, and wherein the boost vaccine is administered no longer than eight weeks after the prime vaccine. Preferably the two shots are given no longer than 6 weeks apart, for example, between 3-6 weeks apart, preferably between 4-6 weeks apart.

The invention further relates to the use of an inactivated equine influenza virus to prepare a boost vaccine for vaccinating equines that have been vaccinated with a priming vaccine containing an attenuated live equine influenza virus, no longer than 8 weeks prior to being vaccinated with the boost vaccine.

It has been found that when equines are vaccinated with such a prime-boost vaccine regimen according to the invention, the equines are protected against clinical signs after a challenge with a virulent equine influenza virus.

Moreover, the equines are completely protected against viral shedding and no virus could be isolated from any vaccinated equines at any time. The prime boost vaccination according to the invention provides sterile immunity, which hitherto, could not be demonstrated for any vaccine against equine influenza. Even when the animals were challenged with a very recent strain of influenza, the prime boost vaccination according to the invention provided sterile immunity against challenge with this recent virus.

The prime vaccine used in the present invention contains the viral pathogen in attenuated live form, meaning that the viral pathogen has been modified in such a way that it does not cause the disease, but still elicits an immune response in the vaccinated animal that attributes to protection against infection with the pathogen. The prime vaccine, comprising an attenuated live equine influenza virus may, for example, contain a temperature sensitive mutant of the equine influenza virus. The prime vaccine further contains the normal constituents of a modified live vaccine, such as a suitable pharmaceutical carrier which is usually a buffered diluent, optionally a preservative, etc., or any other suitable constituent known to the skilled person. The modified live vaccine may be administered via any suitable administration route. If the vaccine is based on a temperature sensitive mutant of the equine influenza virus, for example a ts mutant which only replicated at the (lower) temperatures in the upper respiratory tract, the vaccine is preferably administered via the intranasal route. Cold-adapted equine influenza viruses and vaccines based thereon are, for example, disclosed in U.S. Pat. No. 6,436, 408. An example of a vaccine that can be used as the prime vaccine in the prime-boost regimen according to the invention is the commercially available modified live vaccine Flu Avert I.N. (Heska Corp.)

The boost vaccine comprises an inactivated equine influenza virus.

Vaccines based on inactivated influenza are known in the art. An inactivated vaccine may contain the virus as whole virus (inactivated viral particles) or as subunits (a vaccine containing heamagglutinin and neuraminidase subunits of the virus) in a suitable amount. Suitable amounts of the inactivated virus are known in the art.

An inactivated equine influenza virus may contain an adjuvant. Suitable adjuvants are known in the art. For example, a suitable adjuvant may be based on one or more saponin fractions. Saponin fractions are produced form Quillaja bark extracts (Quil A) (Morein et al., Clin. Immunother., 3(6), 461-475, 1995: "Immunostimulating Complexes, clinical potential in Vaccine Development"). Saponin fractions may be used as such, or in the form of a immunestimulatory complex such as an ISCOM or ISCOM matrix, based on the saponins, a sterol and a lipid. Examples of suitable saponins fractions, and ISCOMs and matrices based thereon are given in Morein et al. (supra) and in WO96/11711. Useful fractions are for example "fraction A" or "Fraction C" of Quil A or mixtures thereof. Good results were obtained when the boost vaccine was the "Equilis Prequenza" vaccine as developed by (Intervet), which is adjuvated with an Iscom matrix based adjuvant.

Either the prime vaccine, or the boost vaccine (or both) may contain, or may be combined with, immunogens derived from, and providing protection against infection with, other pathogens, such as Equine Herpes Virus (EHV-1 and/or EHV4), Equine encephalitis virus (EEE, WEE and/or VEE), West Nile Virus, Tetanus etc. Especially inactivated vaccines (that are used as boost vaccine in the present invention) may contain a combination of antigens derived from different pathogens.

EXAMPLES

Example 1

Comparison of Different Vaccination Schedules

The purpose of this study was to compare different vaccination schedules, using the modified live vaccine Flu avert IN against a challenge with A/equine/2/South-Africa/04/03 considering the recommendation of the OIE to update new influenza vaccines with the South-African strain.

Twenty-four Fjord yearlings were obtained and housed on a pasture.

Seven horses were vaccinated twice with one dose of Flu Avert IN at four weeks interval (group A).

Seven horses were vaccinated with one dose of Flu Avert IN and four weeks later with one dose of Equilis Prequenza Te (group B).

Six horses were vaccinated ones with one dose of Flu Avert IN to determine the onset of immunity (group C).

Four animals were left unvaccinated to serve as control (group D).

Flu Avert IN contains the equine influenza virus strain P821 which is a cold adapted, temperature sensitive mutant of equine influenza type A2 derived from parent virus A/equine/ 2/Kentucky/1/91. The vaccine was registered by Heska Corporation and is distributed in the USA by Intervet inc.

Euqilis Prequenza Te is a suspension for injection containing:

Active Substances:
Purified haemagglutinin subunits from equine influenza viruses:

| A/equine-1/Prague/1/56 | 100 AU (antigenic units) |
| A/equine-2/Newmarket/1/93 | 50 AU |
| A/equine-2/Newmarket/2/93 | 50 AU |

Adjuvant:

| Purified saponins | 375 ug (microgram) |
| Cholesterol | 125 ug |
| Phosphatidylcholine | 62.5 ug |

Excipient

Thiomersal Traces

The vaccine was registered by Intervet International BV.

Three weeks after the second vaccination (groups A and B) or one week after the vaccination (group C) all horses were challenged by aerosol with A/equine-2/South Africa/04/03 virus. After challenge horses were monitored for clinical signs of influenza, body temperature, virus excretion and serology. Blood samples were taken during course of the vaccination and challenge to determine the antibody levels (HI test) against different vaccine strains.

At moment of challenge the horses in group A had a mean HI titre of 6.0 and 5.7 against Newmarket/1/93 and Newmarket/2/93 respectively, the horses in group B had a mean HI titre of 6.1, 11.1 and 10.3 against Prague/1/56, Newmarket/ 1/93 and Newmarket/2/93 respectively. The horses in group C had no HI antibodies at moment of challenge. After challenge all the horses responded well against the Newmarket/1/93 strain, mean HI titres in group A, B, C and D at two weeks after challenge were: 10.9, 10.3, 10.3 and 9.5 respectively.

After challenge the non-vaccinated animals and the horses of group C showed characteristic signs of influenza such as a marked mucopurulent discharge and fever. The vaccinated animals in group A and B showed only mild signs. Virus was isolated from a few horses in group A and from none of the horses of group B. Virus was isolated from all the horses of group C between at 3 days post challenge (dpc) while all the horses of group D shed virus from day 1 till 6 dpc. All parameters examined in the statistical analysis such as the temperature score, the total clinical scores and the duration of virus excretion were significantly lower in the vaccinated animals of group A and B compared to the non-vaccinated group.

It is concluded that the prime boost vaccination course, Flu Avert IN followed by Equilis Prequenza 4 weeks later, strongly reduces clinical signs and induces a sterile immunity when challenged with the recent isolated equine influenza virus strain SA/04/03. Two times Flu Avert with 4 week interval gave also a good protection against SA/04/03 comparable with the protection archived by the recommended basic vaccination course of Equilis Prequenza. Furthermore, the onset of immunity of Flu Avert IN is very rapid, naïve horses were partially protected against SA/04/03 challenge 7 days after the vaccination. It is interesting to investigate the onset of immunity of Flu Avert in previously primed animals.

Example 2

Challenge with Recent Influenza Strain after Prime Boost Vaccination

In a previous study, reflected in Example 1, it was demonstrated that horses showed a sterile immunity when they were primed with the live Flu Avert IN vaccine and boostered 4 weeks later with Prequenza. The purpose of this study was to reconfirm this observation using another challenge virus.

Eight Fjord yearlings were obtained and housed on a pasture. Four horses were vaccinated with one dose of Flu Avert IN and four weeks later with one dose of Equilis Prequenza Te (group A) and four animals were left unvaccinated to serve as control (group B). Three weeks after the second vaccination all horses were challenged by aerosol with A/equine-2/Newmarket/05/03 virus. After challenge horses were monitored for clinical signs of influenza, body temperature, virus excretion and serology. Blood samples were taken during course of the vaccination and challenge to determine the antibody levels (HI test) against different vaccine strains.

At moment of challenge the horses in group A had a mean HI titre of 6.0 and 5.7 against Newmarket/1/93 and Newmarket/2/93 respectively. After challenge all the horses responded well against the Newmarket/1/93 strain, mean HI titres in group A and B at two weeks after challenge were: 10.9 and 9.5 respectively. After challenge the non-vaccinated animals showed characteristic signs of influenza such as a marked mucopurulent discharge, coughing and fever. The vaccinated animals showed only mild signs. No virus was isolated from the vaccinated horses. Virus was isolated from all the control horses between 2 and 6 days post challenge (dpc). All parameters examined in the statistical analysis such as the temperature score, the total clinical scores and the duration of virus excretion were significantly lower in the vaccinated animals compared to the non-vaccinated group.

It is concluded that the prime boost vaccination course, Flu Avert IN followed by Equilis Prequenza 4 weeks later, strongly reduces clinical signs and induces a sterile immunity when challenged with the recent isolated equine influenza virus strain Newmarket/05/03. In general it is clear that when horses that are primed with Flu Avert IN and receive a booster 4 weeks later with Prequenza, a sterile immunity against equine influenza can be archived after challenge.

The invention claimed is:

1. A method for protecting equines against infection with equine influenza comprising, vaccinating an equine with a vaccine containing an attenuated live equine influenza virus and, no longer than 8 weeks later, vaccinating the equine with a booster vaccine comprising an inactivated equine influenza virus.

2. The method according to claim 1, wherein the inactivated vaccine further comprises an adjuvant.

3. The method according to claim 2, wherein the adjuvant is based on an ISCOM matrix.

* * * * *